US005948416A

United States Patent [19]
Wagner et al.

[11] Patent Number: 5,948,416
[45] Date of Patent: *Sep. 7, 1999

[54] STABLE TOPICAL COMPOSITIONS

[75] Inventors: Julie Ann Wagner; Joseph Michael Zukowski, both of Cincinnati; Larry Richard Robinson, Lebanon; George Endel Deckner, Cincinnati, all of Ohio; Marie Antoinette Rinaldi, Petersburg, Fla.; Victoria Claire Szymanski, Loveland, Ohio

[73] Assignee: The Procter & Gamble Company, Cincinnati, Ohio

[ * ] Notice: This patent is subject to a terminal disclaimer.

[21] Appl. No.: 08/647,083

[22] Filed: May 8, 1996

Related U.S. Application Data

[60] Provisional application No. 60/000,673, Jun. 29, 1995, and provisional application No. 60/002,170, Aug. 11, 1995.

[51] Int. Cl.$^6$ ..................................................... A61K 7/48
[52] U.S. Cl. .......................... 424/401; 424/59; 514/844; 514/845; 514/846; 514/847
[58] Field of Search .............................. 424/401, 59, 894, 424/847; 544/844–847

[56] References Cited

U.S. PATENT DOCUMENTS

| | | | |
|---|---|---|---|
| 4,387,090 | 6/1983 | Bolich, Jr. ................................. | 424/70 |
| 4,411,886 | 10/1983 | Hostettler .................................. | 424/70 |
| 4,732,930 | 3/1988 | Tanaka et al. ............................ | 524/742 |
| 4,822,604 | 4/1989 | Knoll et al. ............................... | 424/70 |
| 4,877,805 | 10/1989 | Kligman .................................. | 514/381 |
| 4,888,342 | 12/1989 | Kligman .................................. | 514/419 |
| 4,960,764 | 10/1990 | Figueroa, Jr. et al. ................... | 514/63 |
| 5,073,372 | 12/1991 | Turner et al. ............................. | 424/401 |
| 5,091,171 | 2/1992 | Yu et al. .................................. | 424/642 |
| 5,118,707 | 6/1992 | Chatterjee et al. ....................... | 514/469 |
| 5,238,965 | 8/1993 | Piazza et al. ............................. | 514/844 |
| 5,296,500 | 3/1994 | Hillebrand .............................. | 514/562 |
| 5,385,938 | 1/1995 | Yu et al. .................................. | 514/562 |
| 5,389,677 | 2/1995 | Yu et al. .................................. | 514/557 |
| 5,411,991 | 5/1995 | Shander et al. .......................... | 514/665 |
| 5,534,265 | 7/1996 | Fowler et al. ........................... | 424/489 |
| 5,607,980 | 3/1997 | McAtee et al. .......................... | 514/476 |
| 5,700,452 | 12/1997 | Deckner et al. .......................... | 424/59 |
| 5,720,961 | 2/1998 | Fowler et al. ........................... | 424/401 |
| 5,733,535 | 3/1998 | Hollingshead et al. .................. | 424/65 |
| 5,750,122 | 5/1998 | Evans et al. ............................. | 424/401 |

FOREIGN PATENT DOCUMENTS

| | | |
|---|---|---|
| A2 202621 | 11/1986 | European Pat. Off. . |
| 0 330 369 A1 | 8/1989 | European Pat. Off. . |
| A2 347145 | 12/1989 | European Pat. Off. . |
| 0 384 415 A3 | 8/1990 | European Pat. Off. . |
| 2 594 692 | 8/1987 | France . |
| 92/13566 | 8/1992 | WIPO . |
| 92/19214 | 11/1992 | WIPO . |
| 94/02176 | 2/1994 | WIPO . |
| 95/03781 | 2/1995 | WIPO . |
| 95/24179 | 9/1995 | WIPO . |

OTHER PUBLICATIONS

L. Dai et al., "Preparation of oil–in–water miniemulsions from long–chain fatty alcohols," Chemical Abstracts, vol. 119, No. 14, Oct. 4, 1993, Abstract No. 141638.

R. J. Goetz et al., "Dilute Phase Behavior of Cetyl Alcohol, Sodium Lauryl Sulfate, and Water," Langmuir, vol. 6, 1990, pp. 132–136.

G.H. Dahms et al., "New Formulation Possibilities Offered by Silicone Copolyois," Cosmetics & Toiletries, vol. 110, pp. 91–100, Mar. 1995.

M.E. Carlotti et al., "Optimization of W/O–s Emulsions and Study of the Quantitative Relationships Between Ester Structure and Emulsion Properties," J. Dispersion Science and Technology, 13(3), 315336 (1992).

P. Hameyer, "Comparative Technological Investigations of Organic and Organosilicone Emulsifiers in Cosmetic Water–in–Oil Emulsion Preparations," HAPPI 28(4) 1991, pp. 88–128.

J. Smid–Korbar et al., "Efficiency and usability of silicone surfactants in emulsions," Provisional Communication, International Journal of Cosmetic Science, 12, 135–139 (1990).

D.G. Krzysik et al., "A new Silicone Emulsifier for Water–in–Oil Systems," Drug and Cosmetic Industry, vol. 146(4), pp. 28–81 (Apr. 1990).

G.M. Eccleston, "Multi–phase Oil–in–Water Emulsions," J. Soc. Cosmet. Chem. 41, pp. 1–22 (Jan./Feb. 1990).

W.P. Smith, "Hydroxy Acids and Skin Aging," Walter Smith Consultants, Soap/Cosmetics/Chemical Specialties for Sep. 1993.

G.H. Dahms, "New Oil–in–Water Concepts Based on Emulsifiers derived from Renewable Raw Materials," ICI Surfactants, RP 58/91E.

Dr. P. Loll, "Liquid Crystals in Cosmetic Emulsions" ICI Surfactants, RP 94–93E.

G.H. Dahms, "Properties of O/W Emulsions with Anisotropic Lamellar Phases," Cosmetics & Toiletries, vol. 101, Nov. 1986.

Primary Examiner—Jyothsna Venkat
Attorney, Agent, or Firm—George W. Allen; Loretta J. Henderson

[57] ABSTRACT

The present invention relates to leave on, skin care compositions, comprising: (A) from about 0.001% to about 20% of an active ingredient, (B) from about 1% to about 20% of a stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.; and (C) from about 0.05% to about 10% of a hydrophilic surfactant selected from the group consisting of anionic surfactants, cationic surfactants, zwitterionic surfactants, and mixtures thereof, and (D) from about 25% to about 98.949% water. These compositions are useful for delivering a wide variety of active ingredients to the skin.

20 Claims, No Drawings

STABLE TOPICAL COMPOSITIONS

This application claims benefit of Provisional Application Ser. No. 60/000,673 filed on Jun. 29, 1995 and Provisional Application Ser. No. 60/002,170 filed on Aug. 11, 1995.

TECHNICAL FIELD

The present invention relates to stable, leave-on skin care cosmetic compositions containing an active ingredient. In particular it relates to stable, cosmetic, aqueous-containing compositions having gel networks, liquid crystalline phases, or both. Without being limited by theory, it is believed that the aqueous phase of these compositions contains relatively low levels of free water. In other words, the water is believed to be bound as part of the gel network or liquid crystals. These compositions are useful for delivering a wide variety of active ingredients to the skin.

BACKGROUND OF THE INVENTION

A wide variety of active ingredients are currently known for treating various skin conditions. It is difficult to formulate many of these actives into cosmetically-elegant, oil-in-water systems because of stability, solubility, ionic strength, and other such formulation considerations. Representative of some of these active ingredients are materials such as salicylic acid, N-acetyl-L-cysteine, retinoic acid, phytic acid, and their pharmaceutically-acceptable salts.

For example, cosmetic compositions containing salicylic acid, N-acetyl-cysteine, and retinoic acid are known in the art. Salicylic acid and retinoic acid are keratoylic agents which are believed to help remove keratin plugs and to aid the skin's exfoliation process. These materials are also known for their anti-acne and anti-skin aging benefits. See C. Huber et al., *Arch. Derm Res.* 257, pp. 293–297, 1977; U.S. Pat. No. 4,888,342, to Kligman, issued Dec. 19, 1989; U.S. Pat. No. 4,877,805, to Kligtan, issued Oct. 31, 1989; PCT Application No. US-92-09739, Publication No. 0614354, to R. L. Blank, published Jun. 10, 1993; and PCT Application No. US-92-09737, Publication No.0614353, to R. L. Blank et al., published Jun. 10, 1993, which are all incorporated by reference herein in their entirety. N-acetyl-Lcrysteine is known for regulating wrinkles and skin atrophy (i.e. the thinning and general degradation of the dermis). See U.S. Pat. No. 5,296,500, to Hillebrand, issued Mar. 22, 1994, which is incorporated by reference herein in its entirety.

It has been found that the compositions of the present invention are well-suited for formulating and delivering a wide variety of active ingredients to the skin. Without being limited by theory, it is believed that these compositions contain gel network structures, liquid crystal structure, or both. It is believed that these gel networks and liquid crystals tend to bind the available water in the composition, thereby rendering the water less available for contributing to the instability and decomposition of the active ingredients. It is also found that these compositions are well-suited for carrying a high electrolyte concentration, making them ideal for delivering a wide range of ionic and other highly polar materials, e.g., zinc oxide, polar solvents.

Therefore, it is an object of the present invention to provide novel compositions for delivering a wide variety of active ingredients to the skin.

It is a further object of the present invention to provide water-containing compositions having gel networks, liquid crystals or both.

It is a further object of the present invention to provide water-containing compositions which can accomodate a high electrolyte concentration.

It is a further object of the present invention to provide stable compositions.

It is still a further object of the present invention to provide compositions which have acceptable aesthetic properties.

It is still a further object of the present invention to provide methods of treatment for a wide variety of skin conditions.

SUMMARY OF THE INVENTION

The present invention relates to leave on skin care compositions comprising:
  (A) from about 0.001% to about 20% of an active ingredient;
  (B) from about 1% to about 20% of a hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;
  (C) from about 0.05% to about 10% of a hydrophilic surfactant selected from the group consisting of anionic surfactants, cationic surfactants, zwitterionic surfactants, amphoteric surfactants, and mixtures thereof; and
  (D) from about 25% to about 98.949% water.

All percentages and ratios used herein are by weight of the total composition. All measurements made are at 25° C., unless otherwise designated. The invention hereof can comprise, consist of; or consist essentially of, the essential as well as optional ingredients and components described herein.

DETAILED DESCRIPTION OF THE INVENTION

The cosmetic compositions of the present invention are useful for moisturizing and hydrating the skin and for depositing active ingredients onto the skin. These compositions are in the form of oil-in-water emulsions whereby the oil phase and the water phase can contain, in addition to the essential components described herein, a variety of ingredients known in the art These compositions are in the form of topical, leave-on compositions.

In particular the present invention relates to leave on skin care compositions which are oil-in-water emulsions, comprising:
  (A) from about 0.001% to about 20% of an active ingredient;
  (B) from about 1% to about 20% of a, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;
  (C) from about 0.05% to about 10% of a hydrophilic surfactant selected from the group consisting of anionic surfactants, cationic surfactants, zwitterionic surfactants, amphoteric surfactants, and mixtures thereof; and (D) from about 25% to about 98.949% water.

Preferably the ratio of component (B) to component (C) is from about 20:1 to about 1:1, preferably from about 10:1 to about 1:1, more preferably from about 5:1 to about 1:1, and even more preferably about 3:1. These ratios allow for the formation of lamellar liquid crystalline phases, which contribute to the physical and chemical stability of the composition at temperatures from about −10° C. to about 50° C.

The compositions of the present invention have complex rheological characteristics. These compositions have physical properties characteristic of oil-in-water emulsions, liquid crystals, and crystalline gel networks. Without being limited by theory, it is believed that these compositions have low levels of free water, such that most of the water is bound up with liquid crystals or gel networks. It is found that these compositions are useful as vehicles for compositions which are labile in aqueous solution or dispersion. It is also found that these compositions are useful for formulating actives which present a high electrolyte load for the composition, i.e. actives which are ionic or highly polar.

The nature of liquid crystals, the formation of liquid crystals, the properties and advantages of liquid crystals, and gel networks are described further in G. Dahms, "Properties of O/W Emulsions with Anisotropic Lamellar Phases," 101 *Cosmetics & Toiletries* 113–115, (1986); P. Loll, "Liquid Crystals in Cosmetic Emulsions," *ICI Surfactants' Publication RP*94-93*E*; and G. M. Eccleston, "Multiple-Phase Oil-In-Water Emulsion," 41 *J. Soc. Cosmet. Chem.* 1–22, (January/February 1990); all of which are incorporated herein by reference in their entirety.

The oil-in-water emulsions herein have desirable aesthetic and elegant properties, such as a rich and creamy, yet non-greasy, skin feel. These emulsions can span a broad range of consistencies from thin lotions to heavy creams. These emulsions typically have viscosities ranging from about 100 cps to about 500,000 cps, preferably from about 3,000 cps to about 200,000 cps, more preferably from about 5000 cps to about 150,000 cps, and even more preferably from about 5000 cps to about 100,000 cps, as measured at a temperature of 25° C. with a Brookfield Synchro-Lectric Viscometer Model D. The oil-in-water emulsion compositions can span a wide range of pH values. Even though buffers can be utilized to help maintain the pH of the emulsion compositions, these are not required components, but are merely optional ingredients.

(A) Active Ingredients

The compositions of the present invention comprise a safe and effective amount of one or more active ingredients or pharmaceutically acceptable salts thereof.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgement. What is a safe and effective amount of the active ingredient will vary with the specific active, the ability of the active to penetrate through the skin, the age, health condition, and skin condition of the user, and other like factors.

By "pharmaceutically-acceptable salts" are meant any of the commonly-used salts that are suitable for use in contact with the tissues of humans without undue toxicity, irritation, incompatibility, instability, irritation, allergic response, and the like.

Typically, the actives of the present invention comprise from about 0.001% to about 20%, preferably from about 0.01% to about 10%, and more preferably from about 0.025% to about 5% by weight of the composition.

The actives useful herein can be categorized by their therapeutic benefit or their postulated mode of action. However, it is to be understood that the actives useful herein can in some instances provide more than one therapeutic benefit or operate via more than one mode of action. Therefore, classifications herein are made for the sake of convenience and are not intended to limit the active to that particular application or applications listed. Also, pharmaceutically-acceptable salts of these materials are useful herein. The following actives which preferably have the above outlined solubility parameters are useful in the compositions of the present invention.

Anti-Acne Actives

Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives

Examples of antiwrinkle and anti-skin atrophy actives include retinoic acid and its derivatives (e.g., cis and trans); salicylic acid and derivatives thereof, sulfur-containing D and L amino acids and their derivatives and salts, particularly the N-acetyl derivatives, a preferred example of which is N-acetyl L-gsteine; thiols, eg. ethane thiol; alpha-hydroxy acids, e.g. glycolic acid, and lactic acid; phytic acid, lipoic acid; lysophosphatidic acid, and skin peel agents (e.g., phenol and the like).

Non-Steroidal Anti-Inflammatory Actives (NSAIDS)

Examples of NSAIDS include the following categories: propionic acid derivatives; acetic acid derivatives; fenamic acid derivatives; biphenylcarboxylic acid derivatives; and oxicams. All of these NSADS are filly described in the U.S. Pat. No. 4,985,459 to Sunshine et al., issued Jan. 15, 1991, incorporated by reference herein. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, mniroprofen, tioxaprofen, suprofen, alminoprofen, tiaprofenic acid, fluprofen and bucloxic acid. Also useful are the steroidal anti-inflamnmatory drugs including hydrocortisone and the like.

Tolpical Anesthetics

Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Agents and Accelerators

Examples of artificial tanning agents accelerators include dihydroxyacetone, tyrosine, tyrosine esters such as ethyl tyrosinate, and phospho-DOPA.

Antimnicrobial and Antifungal Actives

Examples of antimicrobial and antifungal actives include β- lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

Sunscreening Actives

Also useful herein are sunscreening agents. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology* all of which are incorporated herein by reference in their entirety. Preferred among those sunscreens which are useful in the compositions of the instant invention are those selected from the group consisting of 2-ethylhexyl p-methoxycinnamate, octyl methoxycinnamate, 1-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylanminobenzoic acid ester of 2,4-hydroxybenzophenone, 4-N,N-(2-ethylhexyl) methylaminobenzoic acid ester with 4-hydroxydibenzoylmethane, 4-N,N-(2-ethylhexyl) methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Preferred examples of actives useful herein include those selected from the group consisting of salicylic acid, 3-hydroxy benzoic acid, 4-hydroxy benzoic acid, acetyl salicylic acid, 2-hydroxybutanoic acid, 2-hydroxypentanoic acid, 2-hydroxyhexanoic acid, cis-retinoic acid, trans- retinoic acid, N-acetyl L-ysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, p-aminobenzoic acid, 2-phenylbenzimnidazole-5-sulfonic acid, dihydroxyacetone, and mixtures thereof.

More preferred examples of actives useful herein include those selected from the group consisting of salicylic acid, acetyl salicylic acid, cis-retinoic acid, trans-retinoic acid, N-acetyl-L-cysteine, lipoic acid, azelaic acid, tetracycline, ibuprofen, naproxen, acetominophen, hydrocortisone, resorcinol, phenoxyethanol, phenoxypropanol, phenoxyisopropanol, 2,4,4'-trichloro-2'-hydoxy diphenyl ether, 3,4,4'-trichlorocarbanilide, octopirox, 2-phenylbenzimidazole-5-sulfonic acid, dihydroxyacetone, and mixtures thereof.

Most preferred examples of actives useful herein include those selected from the group consisting of salicylic acid, cis-retinoic acid, trans-retinoic acid, N-acetyl L-cysteine, azelaic acid, lipoic acid, resorcinol, ibuprofen, naproxen, hydrocortisone, phenoxyethanol, phenoxypropanol, phenoxyisopropanol, 2,4,4'-trichloro-2'-hydroxy diphenyl ether, 3,4,4'-trichlorocarbanilide, 2- phenylbenzimidazole-5-sulfonic acid, dihydroxyacetone, and mixtures thereof.

(B) Structuring Agent

The present invention also comprises from about 1% to about 20%, preferably from about 1% to about 10%, more preferably from about 3% to about 9%, of a stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C. Without being limited by theory, it is believed that these structuring agents are useful to assist in the formation of the rheological characteristic of the composition which contribute to the hydrolytic stability of the composition of the present invention. In particular structuring agents assist in the formation of the liquid crystalline gel network structures.

The preferred structuring agents of the present invention are selected from the group consisting of stearyl alcohol, cetyl alcohol, behenyl alcohol, stearic acid, paimitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. More preferred structuring agents of the present invention are selected from the group consisting of stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof. Even more preferred structuring agents are selected from the group consisting of stearyl alcohol, cetyl alcohol, behenyl alcohol, steareth-2, and mixtures thereof. Most preferred is steareth-2, available under the tradename of Brij® 72 from ICI Americas.

(C) Hydrophilic Surfactant

The compositions of the present invention comprise from about 0.05% to about 10%, preferably from about 1% to about 6%, and more preferably from about 1% to about 3% of at least one hydrophilic surfactant which can disperse the hydrophobic materials in the water phase. The surfactant, at a minimum, must be hydrophilic enough to disperse in water.

The surfactants useful herein can include any of a wide variety of cationic, anionic, zwitterionic, and amphoteric surfactants disclosed in prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

The exact surfactant chosen will depend upon the pH of the composition and the other components present.

Preferred herein are cationic surfactants, especially dialkyl quaternary ammonium compounds. A wide variety of cationic surfactants useful herein are disclosed in U.S. Pat. No. 5,151,209, to McCall et al., issued Sep. 29, 1992; U.S. Pat. No. 5,151,210, to Steuri et al., issued Sep. 29, 1992; U.S. Pat. No. 5,120,532, to Wells et al., issued Jun. 9, 1992; U.S. Pat. No. 4,387,090, to Bolich, issued Jun. 7, 1983;; U.S. Pat. 3,155,591, Hilfer, issued Nov. 3, 1964; U.S. Pat. No. 3,929,678, to Laughlin et al., issued Dec. 30, 1975; U.S. Pat. No. 3,959,461, to Bailey et al., issued May. 25, 1976; *McCutcheon's. Detergents & Emulsifiers*, (North American edition 1979) M.C. Publishing Co.; and Schwartz, et al., *Surface Active Agents, Their Chemistry and Technology*, New York: Interscience Publishers, 1949; all of these documents being incorporated herein by reference in their entirety. The cationic surfactants useful herein include cationic ammonium salts such as those having the formula:

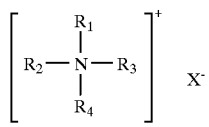

wherein $R_1$, is an allyl group having from about 12 to about 30 carbon atoms, or an aromatic, aryl or alkaryl groups having from about 12 to about 30 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is any compatible anion, preferably selected from the group consisting of chloride, bromide, iodide, acetate, phosphate, nitrate, sulfate, methyl sulfate, ethyl sulfate, tosylate, lactate, citrate, glycolate, and mixtures thereof. Additionally, the alkyl groups of $R_1$, $R_2$, $R_3$, and $R_4$ can also contain ester and/or ether linkages, or hydroxy or amino group substituents (e.g., the allyl groups can contain polyethylene glycol and polypropylene glycol moieties).

More preferably, $R_1$ is an alkyl group having from about 12 to about 22 carbon atoms; $R_2$ is selected from H or an allyl group having from about 1 to about 22 carbon atoms; $R_3$ and $R_4$ are independently selected from H or an allyl group having from about 1 to about 3 carbon atoms; and X is as described previously.

Most preferably, $R_1$ is an alkyl group having from about 12 to about 22 carbon atoms; $R_2$, $R_3$, and $R_4$ are selected from H or an alkyl group having from about 1 to about 3 carbon atoms; and X is as described previously.

Alternatively, other useful cationic emulsifiers include amino-amides, wherein in the above structure $R_1$ is alternatively $R_5CONH-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, behenamidopropyl PG dimonium chloride, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. Especially preferred is behenamidopropyl PG dimonium chloride.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl methyl ammonium bromide, and mixtures thereof. Additional quaternary ammonium salts include those wherein the $C_{12}$ to $C_{30}$ alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the $C_{16}$ to $C_{18}$ range. The term "coconut" refers to an alkyl group derived from a coconut fatty acid, which generally have mixtures of allyl chains in the $C_{12}$ to $C_{14}$ range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-imonium chloride phosphate, stearamidopropyl ethyldimonium ethosultate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof. An example of a quaternary ammonium compound having an alkyl group with an ester linkage is ditallowyl oxyethyl dimethyl ammonium chloride.

More preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, stearamidopropyl PG-dimonium chloride phosphate, stearamindopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Most preferred cationic surfactants are those selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, and mixtures thereof.

A preferred combination of cationic surfactant and structuring agent is behenamidopropyl PG dimonium chloride and/or behenyl alcohol, wherein the ratio is preferably optimized to maintained to enhance physical and chemical stability, especially when such a combination contains ionic and/or highly polar solvents. This combination is especially useful for delivery of sunscreening agents such as zinc oxide and octyl methoxycinnamate.

A wide variety of anionic surfactants are also useful herein. See e.g., U.S. Pat. No. 3,929,678, to Laughlin et al., issued Dec. 30, 1975, which is incorporated herein by reference in its entirety. Nonlimiting examples of anionic surfactants include the alkoyl isethionates, and the alkyl and alkyl ether sulfates. The alkoyl isethionates typically have the formula $RCO—OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1—SO_3—M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-allyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Amphoteric and zwitterionic surfactants are also useful herein. Examples of amphoteric and zwitterionic surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms preferably $C_8$–$C_{18}$) and one contains an anionic water solubilizing group, e.g., carboxy, sulfonate, sulfate, phosphate, or phosphonate. Examples are alkyl imino acetates, and iminodialkanoates and aminoaltanoates of the formulas $RN[CH_2)_mCO_2M]_2$ and $RNH(CH_2)_mCO_2M$ wherein m is from 1 to 4, R is a $C_8$–$C_{22}$ allyl or alkenyl, and M is H, alkali metal, alkaline earth metal ammonium, or alkanolammonium. Also included are imidazolinium and ammonium derivatives. Specific examples of suitable amphoteric surfactants include sodium 3dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-monium chloride phosphate (commercially available as Monaquat PTC, from Mona Corp.).

Also useful herein as amphoteric or zwitterionic surfactants are the betaines. Examples of betaines include the higher allyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Other useful amphoteric and zwitterionic surfactants include the sultaines and hydroxysultaines such as cocamidopropyl hydroxysultaine (available as Miratiane CBS from Rhone-Poulenc), and the alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as anmonium, sodium, potassium and trialkanolamine (e.g., triethanolamine), a preferred example of which is sodium lauroyl sarcosinate.

(D) Water

The compositions of the present invention comprise from about 25% to about 98.949%, more preferably from about 65% to about 95%, and most preferably from about 70% to about 90% water.

Optional Components

Each of the water and oil phases of the emulsions can comprise a wide variety of optional components. Typical of such optional components are:

Alkoxylated Alcohols

The compositions of the present invention comprise from about 0.1% to about 25%, preferably from about 0.1% to about 15%, and more preferably from about 6% to about 10% of an alkoxylated alcohol and/or alkoxylated polyol. The alkoxylated alcohols and polyols useful herein generally are hydrophobic, having a solubility in water of less than about 1 gram per about 100 grams of water at 25° C. Preferably, these solvents have a minimum of 10–20 moles of propylene oxide. These compounds are typically formulated into the oil phase of the oil-in-water emulsions as described in the Examples below. Mixtures of alkoxylated alcohols and polyols can be used herein. The alkoxylated alcohols useful herein can be described by the following general formula:

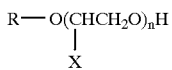

wherein R is selected from the group consisting of alcohols, polyols, diols, and mixtures thereof, having a chainlength of from about 2 to about 30 carbon atoms; n is an integer from about 3 to about 40; X is selected from the group consisting of hydrogen, methyl, ethyl, propyl, and mixtures thereof.

Preferably R is selected from the group consisting of alcohols, polyols, diols, or mixtures thereof, having a chain-length of from about 4 to about 20 carbon atoms; X is methyl; and n is an integer from about 6 to about 35. More preferably R is selected from the group consisting of alcohols, polyols, diols, or mixtures thereof, having a chain-length of from about 4 to about 18 carbon atoms; X is methyl; and n is an integer from about 10 to about 20.

Nonlimiting examples of classes of alkoxylated alcohols useful herein include propoxylated and butoxylated ethers of alcohols and polyols. These compounds can be described as PPG and PBG alkyl ethers wherein the PPG and PBG are commonly used designations for polypropylene glycol and polybutylene glycol, respectively. The average number of PPG or PBG groups in these ethers is commonly given by a number designation after the PPG or PBG. For example, PPG-14 butyl ether, would designate a polypropylene glycol ether of butanol wherein the molecule has on average 14 propylene glycol units.

Nonlimiting examples of alkoxylated alcohols useful herein include PPG-10 butyl ether, PPG-11 butyl ether, PPG-12 butyl ether, PPG-13 butyl ether, PPG-14 butyl ether, PPG-15 butyl ether, PPG-16 butyl ether, PPG-17 butyl ether, PPG-18 butyl ether, PPG-19 butyl ether, PPG-20 butyl ether, PPG-22 butyl ether, PPG-24 butyl ether, PPG-30 butyl ether, PPG-11 stearyl ether, PPG-15 stearyl ether, PPG-10 oleyl ether, PPG-7 lauryl ether, PPG-30 isocetyl ether, PPG-10 glyceryl ether, PPG-15 glyceryl ether, PPG-10 butyleneglycol ether, PPG-15 butylene glycol ether, PPG-27 glyceryl ether, PPG-30 cetyl ether, PPG-28 cetyl ether, PPG-10 cetyl ether, PPG-10 hexylene glycol ether, PPG-15 hexylene glycol ether, PPG-10 1,2,6-hexanetriol ether, PPG-15 1,2,6-hexanetriol ether, and mixtures thereof.

Preferred alkoxylated alcohols are those selected from the group consisting of PPG-14 butyl ether, PPG-15 stearyl ether, PPG-11 stearyl ether, PPG-20 oleyl ether, and mixtures thereof.

More preferred alkoxylated alcohols are those selected from the group consisting of PPG-14 butyl ether, PPG-15 stearyl ether, and mixtures thereof. PPG-14 butyl ether is available under the tradename Fluid AP from Union Carbide Corporation. PPG 15 stearyl ether is available under the tradename Arlamol E from ICI Americas Corporation.

Nonlimiting examples of alkoxylated polyols useful herein include those selected from the group consisting of PPG-10 1,4-butanediol, PPG-12 1,4-butanediol, PPG-14 1,4-butanediol, PPG-2 butanediol, PPG-10 1,6-hexanediol, PPG-12 1,6-hexanediol, PPG-14 hexanediol, PPG-20 hexanediol, and mixtures thereof. Preferred are those selected from the group consisting of PPG-10 1,4-butanediol, PPG-12 1,4-butanediol, PPG-10 1,6-hexandiol, and PPG-12 hexanediol, and mixtures thereof. More preferred is PPG-10 1,4-butanediol. This compound is commercially available under the tradename Macol 57 from PPG/Mazer Corporation.

Polypropylene Glycols

Polypropylene glycols and propylene glycol are useful herein, at a level of from about 1% to about 5% by weight of the composition, preferably from about 2% to about 3.5% by weight of the composition, to enhance the penetration of the acidic active ingredient of the present invention. Polypropylene glycols are polymers which are typically formed from the polymerization of propylene oxide, propylene glycol, propylchlorohydrin, propylbromohydrin, and other related materials. Polypropylene glycols are represented by the following formula:

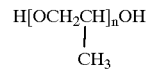

wherein n is an integer from about 10 to about 50, preferably from about 15 to about 40, and more preferably from about 20 to about 34. In the above structure, even though one isomeric orientation is depicted for convenience, this depiction is not intended to preclude other isomeric structures. The polypropylene glycols are commonly designated as PPG's followed by a number indicating the average number of repeating units in the structure. For example, PPG-30 would correspond to the above structure wherein n has an average value of about 30. Based on this nomenclature, the polypropylene glycols useful herein encompass those designated as PPG-10 through PPG-50, more preferably those designated as PPG-15 through PPG40, and most preferably those designated as PPG-20 through PPG-34.

Humectants

Another optional component of the compositions of the present invention is a humectant. When used herein, the humectant can comprise from about 0.1% to about 20%, more preferably from about 0.5% to about 10%, and most preferably from about 1% to about 5% by weight of the composition. Even though these materials are defined herein as humectants, they can also possess moisturizing, skin conditioning, and other related properties.

Examples of humectants useful herein include materials such as urea; guanidine; saturated or unsaturated alkyl alpha hydroxy acids such as glycolic acid and glycolate salts (e.g. ammonium and quaternary allyl ammonium) and lactic acid and lactate salts (e.g. ammonium and quaternary alkyl ammonium); aloe vera in any of its variety of forms (e.g. aloe vera gel); polyhydroxy alcohols such as sorbitol, glycerol, low molecular weight polypropylene glycols (e.g., dipropylene glycol and tripropylene glycol), hexanetriol, propylene glycol, butylene glycol, hexylene glycol, and the like; polyethylene glycol; sugars and starches; sugar and starch derivatives (e.g., alkoxylated glucose); hyaluronic acid; chitin, starch-grafted sodium polyacrylates such as Sanwet (RTM) IM-1000, IM-1500, and IM-2500 (available from Celanese Superabsorbent Materials, Portsmouth, Va.); lactamide monoethanolamine; acetamide monoethanolarnine; propoxylated glycerol (as described in U.S. Pat. No. 4,976,953 to Orr et al., issued Dec. 11, 1990, which is incorporated by reference herein in its entirety); and mixtures thereof.

Preferred humectants useful in the compositions of the present invention are urea, C3–C6 diols and triols, low molecular weight polypropylene glycols, and propoxylated glycerin. Preferred humectants include those materials selected from the group consisting of urea, propylene glycol, 1,3-dihydroxypropane, glycerin, butylene glycol, hexylene glycol, 1,4-dihydroxyhexane, 1,2,6-hexanetriol, dipropylene glycol, tripropylene glycol, and mixtures thereof. More preferred are those selected from the group consisting of urea, glycerin, propylene glycol, hexylene glycol, glycerin, dipropylene glycol, tripropylene glycol, and mixtures thereof. Most preferred is propylene glycol, urea, glycerin, and mixtures thereof.

Emollients

The compositions of the present invention can also include an emollient. Examples of suitable emollients include, but are not limited to, volatile and non-volatile silicone oils (e.g., dimethicone, cyclomethicone, dimethiconol, and the like), highly branched hydrocarbons, and mixtures thereof. Emollients useful in the instant invention are further described in U.S. Pat. No. 4,919,934, to Deckner et al., issued Apr. 24, 1990, which is incorporated herein by reference in its entirety.

The emollients can typically comprise in total from about 0.1% to about 25%, more preferably from about 0.5% to about 10%, and most preferably from about 0.5% to about 5% by weight of the composition.

Additional Ingredients

A variety of additional ingredients can be incorporated into the compositions of the present invention. These additional ingredients, at a minimum, must be acid stable. Non-limiting examples of these additional ingredients include vitamins and derivatives thereof (e.g. tocopherol, panthenol, and the like); other thickening agents (e.g., polyacrylamide and $C_{13}$–$C_{14}$ isoparaffin and laureth-7, available as Sepigel 305 from Seppic Corp., Fairfield, N.J.; and branched polysaccharides such as scleroglucan available under the tradename Clearogel® CS 11 from Michel Mercier Products Inc., Mountainside, N.J.); saturated and/or unsaturated alkyl alpha hydroxy acids; resins; gums (e.g. guar gum, xanthan gum and the like); waxes (both naturally occurring and synthetic); polymers for aiding the film-forming properties and substantivity of the composition (such as a copolymer of eicosene and vinyl pyrrolidone, an example of which is available from GAF Chemical Corporation as Ganex V-220®); abrasive scrub particles for cleansing and exfoliating the skin [e.g., ACuscrub® Mild Abrasives (e.g., ACuscrub® 30, 31, 32, 40, 41, 42, 43, 44, 50, 51, and 52) available from Allied Signal, Inc., Morristown, N.J.; and 3M Brand PMU Capsules microecapsulated mineral oil available from 3M Corporation, St. Paul, Minn.]; preservatives for maintaining the antimicrobial integrity of the compositions; skin penetration aids such as DMSO, 1-dodecylazacycloheptan-2-one (available as Azone® from the Upjohn Co.) and the like; skin bleaching (or lightening) agents including but not limited to hydroquinone, kojic acid and sodium metabisulfite; chelators and sequestrants; and aesthetic components such as fragrances, pigments, colorings, essential oils, skin sensates, astringents, skin soothing agents, skin healing agents and the like, nonlimiting examples of these aesthetic components include panthenol and derivatives (e.g. ethyl panthenol), aloe vera, pantothenic acid and its derivatives, clove oil, menthol, camphor, eucalyptus oil, eugenol, menthyl lactate, witch hazel distillate, allantoin, bisabalol, dipotassium glycyrrhizinate and the like.

Preferred ingredients are saturated and/or unsaturated alkyl alpha hydroxy acids, at a level of from about 0.05% to about 5% by weight of the composition, such as lactic acid, lactate salts (e.g. ammonium and quaternary alyl ammonium), glycolic acid, glycolate salts (e.g. ammonium and quaternary allyl ammonium), and fruit acids. A discussion of alpha hydroxy acids is disclosed in Walter P. Smith, Hydroxy Acids and Skin Aging, *Soap/Cosmetics/Chemical Specialties*. pp. 54–59, (September 1993), which is herein incorporated by reference in its entirety.

Methods of Treatment

The present invention also relates to methods wherein an effective amount of the active ingredient is deposited on the skin in order to modify the condition being treated or to deliver the desired benefit. An effective amount is an adequate amount to deliver the desired benefit but low enough to avoid serious side effects at a reasonable benefit to risk ratio within the scope of sound medical judgement. What is a safe and effective amount of the acidic active will vary with the specific active, the ability of the active to penetrate through the skin, the age of the user, the health condition of the user, the skin condition of the user, and other like factors. Such methods comprise topically applying to the skin or scalp, an effective amount of the composition of the present invention. The composition can be applied for several days in a row, weeks, months or years at an appropriate interval. Appropriate intervals are from about three times daily to about one time every three days, preferably from about two times daily to about one time every other day, more preferably about one time daily, until satisfactory results are achieved. A wide range of quantities of the compositions of the present invention can be employed to provide a benefit. Quantities of the present compositions which are typically applied to provide a benefit can range form about 0.1 $mg/cm^2$ to about 10 $mg/cm^2$. A particularly useful amount to use is about 2 $mg/cm^2$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Examples I–II

Leave on Moisturizing Compositions

Leave on moisturizing, oil-in-water emulsions are prepared by combining the following ingredients using conventional mixing techniques as described below.

| Ingredient | I WT. % | II WT. % |
|---|---|---|
| Salicylic Acid | 2 | 1.5 |
| PPG-14 Butyl Ether | 8.00 | 8.00 |
| Glycerin | 4.00 | 4.00 |
| Stearyl Alcohol | 1.5 | 1.5 |
| Cetyl Alcohol | 3.00 | 3.00 |
| Distearyl Dimethyl Ammonium Chloride | 0.1 | 0.1 |
| Propylene Glycol | 3.00 | 3.00 |
| Steareth-21[1] | 2.0 | 2.0 |
| Steareth-2[2] | 1.0 | 1.0 |
| Dimethicone[3] | 1.0 | 1.0 |
| Cyclomethicone[4] | 1.0 | 1.0 |
| Disodium EDTA | 0.02 | 0.02 |
| Minors | 0.07 | 0.07 |
| Water | QS 100 | QS 100 |

[1]polyethylene glycol ether of stearyl alcohol with an average of about 21 moles of ethylene oxide.
[2]Polyethylene glycol ether of stearyl alcohol with an average of about 2 moles of ethylene oxide.
[3]A mixture of fully methylated linear siloxane polymers end blocked with trimethyldiloxy units.
[4]A cyclic dimethyl polysiloxane compound.

The above compositions are prepared as follows:

First prepare a water phase by heating the water to a temperature of about 180° F. (82° C.) and adding the distearyl dimethyl ammonium chloride, glycerin, and propylene glycol. Keep this mixture at a temperature of from about 65° C. to about 75° C.

In a separate vessel prepare the oil phase by mixing the cetyl alcohol, stearyl alcohol, steareth-2, steareth-21, the dimethicone, and the cyclomethicone and heating the mixture to a temperature of from about 65° C. to about 75° C.

In a separate vessel prepare the salicylic acid phase by mixing the salicylic acid into the PPG-14 butyl ether at a temperature of from about 65° C. to about 75° C.

Thereafter, mix the salicylic acid phase into the oil phase at a temperature of from about 65° C. to about 75° C. Add the oil phase mixture to the water phase mixture and mill at a temperature of from about 65° C. to about 75° C. Cool the resulting mixture to a temperature of from about 40° C. to about 50° C. Thereafter, add a mixture comprising the minor ingredients and the disodium EDTA to the emulsion. Cool to ambient temperature. In the alternative the above compositions can be prepared as follows:

First prepare a water phase by heating the water to a temperature of about 180° F. (82° C.) and adding the distearyl dimethyl anmonium chloride, glycerin, propylene glycol, cetyl alcohol, stearyl alcohol, steareth-2, and steareth-21. Keep this mixture at a temperature of from about 65° C. to about 75° C.

In a separate vessel prepare the salicylic acid phase by mixing the salicylic acid, PPG-14 butyl ether, the dimethicone, and the cyclomethicone at a temperature of from about 65° C. to about 75° C.

Thereafter, mix the salicylic acid phase mixture into the water phase mixture and mill at a temperature of from about 65° C. to about 75° C. Cool the resulting mixture to a temperature of from about 40° C. to about 50° C. Thereafter, add a mixture comprising the minor ingredients and the disodium EDTA to the emulsion. Cool to ambient temperature.

The resulting compositions are useful for application to the skin for delivering the acid active are useful for treating wrinkles, dry skin and other age-related conditions of the skin. These compositions demonstrate good stability.

In further embodiments compositions are prepared in which the salicylic acid is replaced with 0.025% retinoic acid and 0.5% N-acetyl-L-cysteine, respectively, with the water levels being adjusted accordingly.

Example III

Leave on Composition

A leave on compositions containing N-acetyl-L-cysteine as the active ingredient is prepared by combining the following ingredients using conventional mixing techniques as described below.

| Ingedient | Weight % |
|---|---|
| Water | QS 100 |
| PPG-15 Stearyl Ether | 3.25 |
| Glycerin | 3.0 |
| Stearyl Alcohol | 2.028 |
| Steareth-2 | 1.097 |
| Polyethylene[1] | 1.0 |
| Dimethicone[2] | 1.0 |
| Distearyl Dimethyl Ammonium Chloride | 0.95 |
| Cyclomethicone (and) Dimethiconol[3] | 0.75 |
| Sodium Hydroxide | 0.58 |
| Cetyl Alcohol | 0.559 |
| N-Acetyl-L-Cysteine | 0.50 |
| Benzyl Alcohol | 0.50 |
| Steareth-21 | 0.366 |
| Methyl Paraben | 0.25 |
| Behenyl Alcohol | 0.221 |
| Fragrance | 0.20 |
| Citric Acid | 0.19 |
| Disodium EDTA | 0.13 |
| Propyl Paraben | 0.10 |
| Zinc Oxide | 0.025 |

[1]Low density polyethylene powder available from U.S. Industrial Chemical as MN-714 and MN-722.
[2]Available as Dow Corning 10 Centistoke dimethicone fluid from Dow Corning Corporation.
[3]Available as Dow Corning Q2-1401 fluid from Dow Corning Corporation.

The above composition is prepared as follows:

A water phase is prepared by combining about 90% of the water, glycerin, methyl paraben, and disodium EDTA and heating to 70–75° C. Next, an oil phase is prepared by combining the PPG-15 stearyl ether, stearyl alcohol, steareth-2, distearyl dimethyl ammonium chloride, cetyl alochol, stearth-21, behenyl alcohol, propyl paraben and heating to 70–75° C. The oil phase is mixed into the water phase with stirring, and the resulting mixture is flash-cooled with stirring to 35–40° C. Next, the remaining water, N-acetyl-L-cysteine, citric acid, and zinc oxide are combined and added to the mixture with stirring. The remaining ingredients are then added with stirring.

The resulting composition is useful for application to the skin for delivering the active and to treat and improve the appearance of the skin.

Examples IV–V

Sunscreening Composition

Sunscreening compositions containing zinc oxide and octyl methoxycinnamate as the active ingredient is prepared by combining the following ingredients using conventional mixing techniques as described above.

| Ingredient | I WT. % | II WT. % |
| --- | --- | --- |
| Octyl methoxycinnamate | 6.0 | 7.5 |
| Zinc Oxide | 5.0 | 10.0 |
| Isohexadecane | 4.0 | 3.0 |
| Glycerin | 3.00 | 5.0 |
| Steareth-2 | 1.5 | 2.0 |
| Stearyl alcohol | 1.5 | 1.5 |
| Behenyl alcohol | 1.25 | 1.5 |
| Cetyl alcohol | 0.00 | 2.00 |
| Benzyl alcohol | 0.50 | 0.50 |
| Behenamidopropyl PG dimonium chloride | 0.30 | 1.00 |
| Methylparaben | 0.25 | 0.25 |
| Propyl paraben | 0.15 | 0.15 |
| Disodium EDTA | 0.10 | 0.10 |
| Water | QS 100 | QS 100 |

What is claimed is:

1. A leave on skin care composition, comprising, by weight:
   (A) from about 0.001% to about 20% of an active ingredient;
   (B) from about 3% to about 20% of a hydrophobic structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;
   (C) from about 0.05% to about 3% of surfactant consisting essentially of a hydrophilic cationic surfactant selected from the group consisting of behenamidopropyl PG dimonium chloride, dilauryl dimethyl ammonium chloride, distearyl dimethyl ammonium chloride, dimyristyl dimethyl ammonium chloride, dipalmityl dimethyl ammonium chloride, stearamidopropyl PG dimonium chloride phosphate, stearamidopropyl ethyldiammonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof;
   (D) from about 6% to about 15% of an alkoxylated alcohol or alkoxylated polyol; and
   (E) from about 70% to about 90% water.

2. The composition of claim 1 wherein the active ingredient is selected from the group consisting of salicylic acid, acetyl salicylic acid, cis-retinoic acid, trans-retinoic acid, N-acetyl-L-cysteine, lipoic acid, azelaic acid, phytic acid, lisophosphotidic acid, tetracycline, ibuprofen, naproxen, acetominophen, hydrocortisone, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-phenylbenzimidazole-5-sulfonic acid, dihydroxyacetone, pharmaceutically-acceptable salts thereof, and mixtures thereof.

3. The composition of claim 1 wherein the active ingredient is selected from the group consisting of salicylic acid, retinoic acid, N-acetyl-L-cysteine, lipoic acid, pharmaceutically-acceptable salts thereof, and mixtures thereof.

4. The composition of claim 3 wherein the level of active is from about 0.01% to about 10% by weight of the composition.

5. The composition of claim 3 wherein the level of active is from about 0.025% to about 5% by weight of the composition.

6. The composition of claim 5 wherein the hydrophobic structuring agent is selected from the group consisting of stearyl alcohol, cetyl alcohol, behenyl alcohol, stearic acid, palmitic acid, polyethylene glycol ether of stearyl alcohol having an average of about 2 ethylene oxide units, and mixtures thereof.

7. The composition of claim 1 wherein the cationic surfactant is selected from the group consisting of dilauryl dimethyl ammonium chloride, distearyl dimethyl ammonium chloride, dimyristyl dimethyl ammonium chloride, dipalmityl dimethyl ammonium chloride, and mixtures thereof.

8. A method for treating skin comprising applying the composition of claim 1.

9. A The composition of claim 1, wherein the weight ratio of component (B) to component (C) is from about 20:1 to about 1:1.

10. The composition of claim 1, wherein the weight ratio of component (B) to component (C) is from about 10:1 to about 1:1.

11. The composition of claim 1, wherein the weight ratio of component (B) to component (C) is from about 5:1 to about 1:1.

12. The composition of claim 1, comprising, by weight, from about 0.01% to about 10% of the active ingredient, from about 3% to about 10% of the hydrophobic structuring agent, from about 0.05% to about 10% of the cationic surfactant, and from about 70% to about 95% water.

13. The composition of claim 1, comprising, by weight, from about 6% to about 10% of the alkoxylated alcohol or the alkoxylated polyol.

14. A leave on skin care composition, comprising by weight:
   (A) from about 0.001% to about 20% of an active ingredient selected from the group consisting of benzoyl peroxide, 2,4,4'-trichloro-2-hydroxy diphenyl ether, phenoxyethanol, phenoxypropanol, phenoxyisopropanol, phytic acid, lipoic acid, lisophosphatidic acid, benoxaprofen, flubiprofen, fenoprofen, fenbufen, ketoprofen, indoprofen, priprofen, carprofen, oxaprozin, pranoprofen, miroprofen, tioxaprofen, suprofen, alminoprofen, tiaprofenic acid, fluprofen, bucloxic acid, benzocaine, lidocaine, bupivacaine, chloroprocaine, dibucaine, etidocaine, mepivacaine, tetracaine, dyclonine, hexylcaine, procaine, cocaine, ketamine, pramoxine, phenol, dihydroxyacetone, tyrosine, ethyltryosinate, phospho-DOPA, β-lactim drugs, quinoline drugs, ciprofloxacin, norfloxacin, erythromycin, amikacin, doxycycline, capreomycin, chlorhexidine, chlortetracycline, oxytetracycline, clindamycin, ethambutol, hexamidinee isethionate, metronidazole, pentamidine, , gentamicin, kanamycin, lineomycin, methacyclin, methenamine, minocycine, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxyclcyline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amnanfadine sulfate, octopirox, parachlorometa xylenol, nystatin, tolnaftate, clotrimazole, 2-ethylhexyl p-methoxycinnamate, octyl methoxycinnamate, p-amino benzoate, p-aminobenzoic acid, 2-phenyl benzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, silica, iron oxide, 4-N,N-(2-ethylhexyl)methyl aminobenzoic acid ester of 2,4-dihydroxybenzophenone, 4-N,N-(2-ethylhexyl)methyl aminobenzoic acid ester with 4-hydroxydibenzoylmethane, 4-N,N-(2-ethylhexyl) methyl aminobenzoic acid ester of 2-hydroxy-4-(2-hydroxyethoxy)benzophenone, 4-N,N-(2-ethylhexyl)-methyl aminobenzoic acid ester of 4-(2-hydroxyethoxy)dibenzoylmethane, tetracycline, ibuprofen, naproxen, acetaminophen, resorcinol, 3,4, 4'-trichlorocarbanilide, octopirox, pharmaceutically-acceptable salts thereof, and mixtures thereof;

(B) from about 1% to about 20% of a hydrophobic structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45° C.;

(C) from about 0.05% to about 10% of surfactant consisting essentially of a hydrophilic cationic surfactant;

(D) from about 0.1% to about 15% of an alkoxylated alcohol or alkoxylated polyol; and (E) from about 25% to about 95% water.

15. The composition of claim 14, wherein the active ingredient is selected from the group consisting of lipoic acid, phytic acid, lisophosphotidic acid, tetracycline, ibuprofen, neoprene, acetaminophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, 2-phenylbenzimidalole-5-sulfonic acid, dihydroxyacetone, pharmaceutically-acceptable salts thereof, and mixtures thereof.

16. The composition of claim 14, comprising, by weight, from about 0.01% to about 10% of the active ingredient, from about 3% to about 10% of the hydrophobic structuring agent, from about 0.05% to about 3% of the surfactant consisting essentially of hydrophilic cationic surfactant, and from about 70% to about 95% water.

17. The composition of claim 14, further comprising, by weight, from about 0.1% to about 15% of an alkoxylated alcohol or alkoxylated polyol.

18. The composition of claim 1, wherein the hydrophobic structuring agent comprises behenyl alcohol and the hydrophilic cationic surfactant comprises behenamidopropyl PG dimonium chloride.

19. The composition of claim 18, wherein the active ingredient comprises zinc oxide or octyl methoxycinnamate.

20. The composition of claim 1, wherein the hydrophobic structuring agent is selected from the group consisting of stearyl alcohol, cetyl alcohol, behenyl alcohol, stearic acid, palmitic acid, polyethyleneglycol ethers of stearyl alcohol, and mixtures thereof.

* * * * *

UNITED STATES PATENT AND TRADEMARK OFFICE
CERTIFICATE OF CORRECTION

PATENT NO. : 5,948,416  
DATED : September 7, 1999  
INVENTOR(S) : Julie Ann Wagner et al.

Page 1 of 4

It is certified that error appears in the above-identified patent and that said Letters Patent is hereby corrected as shown below:

At column 1, line 11 "aqueons" should read --aqueous--.

At column 1, line 30 "N-acetyl-cysteine" should read --N-acetyl-L-cysteine--.

At column 1, line 38 "Kligtan" should read --Kligman--.

At column 1, lines 43-44 "N-acetyl-Lcrysteine" should read --N-acetyl-L-cysteine--.

At column 2, line 36 "consist of; or" should read --consist of, or--.

At column 2, line 48 "art These" should read --art. These--.

At column 4, line 34 "thereof, sulfur" should read --thereof; sulfur--.

At column 4, line 37 "L-gsteine" should read --L-cysteine--.

At column 4, line 45 "NSADS are filly" should read --NSAIDS are fully--.

At column 4, line 51 "mniroprofen" should read --miroprofen--.

At column 4, line 53 "anti-inflamnmatory" should read --anti-inflammatory--.

At column 4, line 55 "Tolpical" should read --Topical--.

At column 4, line 65 "Antimnicrobial" should read --Antimicrobial--.

At column 5, line 32 "*Technology* all" should read --*Technology*, all--.

At column 5, line 58 "methylanminobenzoic" should read --methylaminobenzoic--.

At column 5, line 59 "hydroxybenzophenone" should read --dihydroxybenzophenone--.

UNITED STATES PATENT AND TRADEMARK OFFICE
CERTIFICATE OF CORRECTION

PATENT NO. : 5,948,416
DATED : September 7, 1999
INVENTOR(S) : Julie Ann Wagner et al.

It is certified that error appears in the above-identified patent and that said Letters Patent is hereby corrected as shown below:

At column 6, line 12 "L-ysteine" should read --L-cysteine--.

At column 6, line 19 "phenylbenzimnidazole" should read --phenylbenzimidazole--.

At column 6, line 27 "hydoxy" should read --hydroxy--.

At column 6, line 59 "paimitic" should read --palmitic--.

At column 7, line 37 "May. 25" should read --May 25--.

At column 7, line 38 "*McCutcheon's. Detergents*" should read --*McCutcheon's, Detergents*--.

At column 7, line 53 "allyl group" should read --alkyl group--.

At column 7, line 65 "allyl groups" should read --alkyl groups--.

At column 8, line 3 "allyl group" should read --alkyl group--.

At column 8, line 4 "an allyl" should read --an alkyl--.

At column 8, line 55 "allyl chains" should read --alkyl chains--.

At column 8, line 64 "di(coconutalkyl)dimethyl" should read --di(coconutalkyl)dimethyl--.

At column 8, line 66 "PG-imonium" should read --PG-dimonium--.

At column 8, line 67 "ethosultate" should read --ethosulfate--.

At column 9, lines 14-15 "stearamindopropyl" should read --stearamidopropyl--.

At column 9, line 15 "ethossulfate" should read --ethosulfate--.

UNITED STATES PATENT AND TRADEMARK OFFICE
CERTIFICATE OF CORRECTION

PATENT NO. : 5,948,416

DATED : September 7, 1999

INVENTOR(S) : Julie Ann Wagner et al.

It is certified that error appears in the above-identified patent and that said Letters Patent is hereby corrected as shown below:

At column 9, line 63 "b-allyloxy" should read --b-alkyloxy--.

At column 10, line 15 "atoms preferably" should read --atoms (preferably--.

At column 10, lines 18-19 "aminoaltanoates" should read --aminoalkanoates--.

At column 10, line 20 "allyl" should read --alkyl--.

At column 10, line 24 "3dodecyl" should read --3-dodecyl--.

At column 10, line 35 "PG-monium" should read --PG-dimonium--.

At column 10, line 40 "higher allyl" should read --higher alkyl--.

At column 10, line 61 "anmonium" should read --ammonium--.

At column 12, line 48 "PPG40" should read --PPG-40--.

At column 12, line 63 "allyl ammonium" should read --alkyl ammonium--.

At column 13, lines 8-9 "monoethanolamine" should read --monoethanolamine--.

At column 14, line 15 "quaternary alyl" should read --quaternary alkyl--.

At column 14, line 17 "quaternary allyl" should read --quaternary alkyl--.

At column 14, line 20 "*Specialties*. pp." should read --*Specialties*, pp.--.

At column 15, line 19 "stearyI alcohol" should read --stearyl alcohol--.

At column 15, line 48 "anmonium" should read --ammonium--.

UNITED STATES PATENT AND TRADEMARK OFFICE
CERTIFICATE OF CORRECTION

PATENT NO. : 5,948,416
DATED : September 7, 1999
INVENTOR(S) : Julie Ann Wagner et al.

It is certified that error appears in the above-identified patent and that said Letters Patent is hereby corrected as shown below:

At column 18, line 18 "A The composition" should read --The composition--.
At column 18, line 35 "comprising by" should read --comprising, by--.
At column 18, line 39 "2,4,4'-trichloro-2-hydroxy" should read --2,4,4'-trichloro-2"-hydroxy--.
At column 18, line 54 "hexamidinee" should read --hexamidine--.
At column 18, line 56 "minocycine" should read --minocycline--.
At column 19, lines 5-6 "amnanfadine" should read --amanfadine--.

Signed and Sealed this

Eleventh Day of July, 2000

*Attest:*

Q. TODD DICKINSON

*Attesting Officer*   *Director of Patents and Trademarks*